United States Patent [19]

Yih

[11] Patent Number: 4,806,682
[45] Date of Patent: Feb. 21, 1989

[54] SULFONIUM SALTS OF DIPHENYL ETHERS

[75] Inventor: Roy Y. Yih, Doylestown, Pa.

[73] Assignee: Rohm and Haas Company, Philadelphia, Pa.

[21] Appl. No.: 945,171

[22] Filed: Dec. 22, 1986

Related U.S. Application Data

[63] Continuation of Ser. No. 419,360, Sep. 17, 1982, abandoned.

[51] Int. Cl.$^4$ .............................................. C07C 65/00
[52] U.S. Cl. ..................................... 562/474; 71/103; 558/414; 558/416; 562/434; 560/55; 560/23
[58] Field of Search .................. 562/474, 434; 71/103; 558/414, 416; 560/55, 23

[56] References Cited

U.S. PATENT DOCUMENTS

| | | | |
|---|---|---|---|
| 3,282,991 | 11/1966 | Klein et al. | 260/501 |
| 3,813,444 | 5/1974 | Abe et al. | |
| 3,928,416 | 12/1975 | Bayer et al. | |
| 3,929,455 | 12/1975 | Theissen | |
| 4,015,975 | 4/1977 | Tamura et al. | |
| 4,017,300 | 4/1977 | Rohe et al. | |
| 4,063,929 | 12/1977 | Bayer et al. | |
| 4,315,765 | 2/1982 | Large | |

FOREIGN PATENT DOCUMENTS 0003416 8/1979 European Pat. Off. .

*Primary Examiner*—Paul J. Killos
*Attorney, Agent, or Firm*—Barbara V. Maurer

[57] ABSTRACT

Sulfonium and sulfoxonium salts of the formula

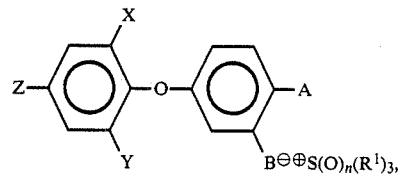

wherein X and Y are independently a hydrogen atom, a halogen atom, a trihalomethyl group, a nitro group, an alkyl group or a cyano group; Z is a halogen atom, a trihalomethyl group, an alkyl group, cyano group or —S(O)$_m$R, wherein m is 0, 1 or 2 and R is an alkyl group; A is a halogen atom, a nitro group or a cyano group; B is a negatively charged organic substituent; n is 0 or 1, each R$^1$ is independently an alkyl group, an aryl group or —N(R$^2$)$_2$ wherein R$^2$ is an alkyl group or an aryl group; S is sulfur; and N is nitrogen, and compositions containing these salts exhibit herbicidal activity.

32 Claims, No Drawings

SULFONIUM SALTS OF DIPHENYL ETHERS

This application is a continuation of application Ser. No. 419,360, filed Sept. 17, 1982.

TECHNICAL FIELD

This invention relates to novel compounds which are sulfonium or sulfoxonium, including amino sulfoxonium, salts of diphenyl ethers, to compositions containing these salts and to their use as herbicides.

BACKGROUND ART AND PRIOR ART STATEMENT

A number of diphenyl ethers and their metal or ammonium salts have shown to be effective weed control agents. For example, alkali, alkaline earth and transition metal salts and ammonium salts of 2,6-substituted-4-trifluoromethyl-3,-substituted-4'-nitro diphenyl ethers (U.S. Pat. No. 3,928,416 and U.S. Pat. No. 4,063,929) and substituted-phenyl-3'-carboxy salt -4'-nitro phenyl ethers (U.S. Pat. No. 3,929,455) are known to have herbicidal activity. Para-nitro diphenyl ethers (U.S. Pat. No. 3,813,444) and 4-trifluoromethyl-diphenyl ethers (U.S. Pat. No. 4,017,300) which contain an alkylthio, an alkylsulfinyl or alkylsulfonyl substituent are known as herbicides as are alkyl-2-nitro-5-(2',4'-dichlorophenoxy)-thiobenzoates (U.S. Pat. No. 4,015,975).

Trialkylsulfonium salts of N-phosphonomethylglycine, a totally different class of compounds than diphenyl ethers, have been taught as having plant growth regulation and herbicidal activity (U.S. Pat. No. 4,315,765). It is the discovery, however, of this invention that trialkylsulfonium and trialkylsulfoxonium salts of certain diphenyl ethers, as described herein, are effective as herbicides.

DESCRIPTION OF THE INVENTION

In accordance with the present invention, there is provided a new class of diphenyl ethers which are sulfonium or sufoxonium salts of the formula

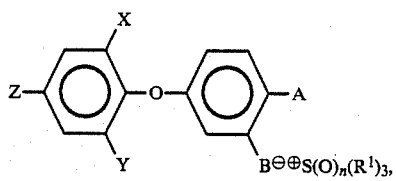

(I)

wherein:

X and Y are independently a hydrogen atom, a halogen atom, preferably a chlorine or bromine atom, a trihalomethyl group, preferably trifluoromethyl group, a nitro group, an alkyl group, preferably having 1 to 4 carbon atoms, or a cyano group; preferably X is a halogen atom or a trihalomethyl group and Y is a hydrogen atom, a halogen atom or a trihalomethyl group and more preferably X is a halogen atom and Y is a hydrogen atom or a halogen atom;

Z is a halogen atom, a trihalomethyl group, preferably a trifluoromethyl group, an alkyl group, preferably having 1 to 4 carbon atoms, a cyano group or —S-(O)$_m$R$^2$ wherein m is 0, 1 or 2 and R$^2$ is an alkyl group, preferably a (C$_1$–C$_4$)alkyl, preferably Z is a halogen atom or a trihalomethyl group, more preferably a trihalomethyl group, and most preferably trifluoromethyl;

A is a halogen atom, a nitro group or a cyano group, preferably a halogen atom or a nitro group and more preferably a nitro group;

B is a negatively charged organic substituent which allows for the formation of a sulfonium or sulfoxonium salt;

S is sulfur;

N is nitrogen;

n is 0 or 1;

R$^1$ is independently an alkyl group, preferably a (C$_1$–C$_4$)alkyl group, an aryl group, preferably a phenyl or naphthyl group and more preferably a phenyl group, or —N(R$^2$)$_2$ wherein R$^2$ is an alkyl group, preferably a (C$_1$–C$_4$)alkyl group, or an aryl group, preferably a phenyl or naphthyl group and more preferably a phenyl group.

Examples of B substituents include a carboxy group, —COO$^\ominus$, a sulfonamide group, —C(O)N$^\ominus$SO$_2$R$^3$, and organic moieties of R$^3$ substituted with a carboxy group, —R$^3$CO$_2{}^\ominus$, and/or a sulfonamide group, —R$^3$-C(O)NSO$_2$R$^3$, wherein R$^3$ is an organic radical containing an alkyl group, alkenyl group, alkynyl group, alkylamino group, alkoxy group, aryl group, alkylaryl group, carbalkyl group, hydroxyalkyl group, alkoxyalkyl group, haloalkyl group, aryl group, a substituted aryl group or a substituted alkylaryl group, having up to two and preferably up to one substitution, wherein the substitution is a halogen atom, a trihalomethyl group, a cyano group, a nitro group, a carboxyalkyl group, an alkoxy group, an alkyl group, an alkenyl group, an alkynyl group, a thioalkyl group, a phosphite group and/or an amino group. R$^3$ can be comprised of a combination of the aforementioned organic groups, preferably a combination of up to two organic groups, except those combinations which would be readily apparent to one in the art as being chemically unstable, e.g., an alkoxy or alkylamino wherein the heteroatom is attached to a terminal carboxy group, —CH$_2$NCOO$^\ominus$ or —CH$_2$OCOO$^\ominus$, or a carbonyl group beta to a terminal carboxy group, —COCH$_2$COO$^\ominus$. The B substituents, and thus the R$^3$ organic radicals, which render the diphenylethers of this invention more water soluble are more preferred.

The terms "alkyl", "alkenyl", 37 alkoxy" and "alkynyl", as used to describe the substituents on the diphenyl ether, refer to branched or straight chained carbon moieties having from 1 to 8 total carbon atoms with the straight chain portion of the moiety comprising from 1 to 6 and preferably from 1 to 4 carbon atoms. Additionally, the term "alkoxy", as used to describe the B substituent, is intended to include both unsubstituted and substituted alkoxy groups which have one or more hydrogen atoms replaced by a substituent group such as halogen or a trihaloalkyl group, preferably trifluoromethyl.

The term "aryl" as used to describe any portion of the diphenyl ether refers preferentially to a phenyl or naphthyl and more preferentially to a phenyl group.

Examples of the compounds embraced by Formula I include:

Trimethyl sulfonium-5-(2-chloro-4-trifluoromethylphenoxy)-2-nitro benzoate,

Trimethyl sulfoxonium-5-(2-chloro-4-trifluoromethylphenoxy)-2-nitro benzoate,

Trimethyl sulfonium-5-(2-chloro-4-trifluoromethylphenoxy)-2-nitro-N-methanesulfonyl benzamide, Trimethyl sulfonium-2-[5-(2-chloro-4-trifluoromethylphenoxy)-2-nitrophenoxy]acetate, Trimethyl sulfonium-3-[5-(2-chloro-4-trifluoromethyl-phenoxy)-2-nitro-phenyl amino]propionate,
Trimethyl sulfonium-2-chloro-4-trifluoromethyl-3'[1-(carboxy)-ethoxycarbonyl]-4'-nitro diphenyl ether,
Triethyl sulfonium-2-chloro-4-trifluoromethyl-3'-[1(carboxy)-methoxycarbonyl]-4'-nitro diphenyl ether,
Trimethyl sulfonium-2-chloro-4-trifluoromethyl-3'-[2-(carboxy)-ethoxycarbonyl]-4'-nitro diphenyl ether,
Trimethyl sulfonium-N-[5-(2-chloro-4-trifluoromethyl-phenoxy)-2-nitrophenoxy]alanine,
Trimethyl sulfonium-N-[5-(2,6-dichloro-4-trifluoromethylphenoxy)-2-nitro]benzoate,
Trimethyl sulfonium-5-(2-chloro-4-trifluoromethyl-phenoxy)-2-bromo benzoate,
Trimethyl sulfonium-5-(2,6-dichloro-4-trifluoromethyl-phenoxy)-2-chloro benzoate,
Trimethyl sulfoxonium-5-(2,6-dichloro-4-trifluoromethylphenoxy)-2-chlorobenzoate,
Trimethyl sulfonium-5-(2,4-dichloro-phenoxy)-2-nitro benzoate,
Trimethyl sulfoxonium-5-(2,4,6-trichloro phenoxy)-2-nitro benzoate,
Trimethyl sulfoxonium-5-[2-chloro-4-(methane sulfonyl)phenoxy]-2-nitro benzoate,
Triethyl sulfonium-5-(2-trifluoromethyl-4-cyanophenoxy)-2-nitro-N-methanesulfonyl benzamide,
Methyl diphenyl sulfonium-3-5-(2-chloro-4trifluoromethylphenoxy)-2-bromo benzoyl]-N-methanesulfonyl propionamide,
Phenylmethyldimethylamino sulfonium-3-[5-(2cyano-4-trifluoromethylphenoxy)-2chlorophenyl]propionate,
Trimethyl sulfonium-beta-[5-(2-chloro-4-trifluoromethylphenoxy)-2-nitro phenyl]acrylate,
Triethyl sulfonium-2-[5-(2-chloro-4trifluoromethyl-phenoxy)-2-bromo phenoxy]-2-methoxy acetate,
Diphenyl methyl sulfonium-3-[5-(2-fluoro-4-trifluoromethylphenoxy)-2-nitro phenoxy methylene]-benzoate,
Triethyl sulfonium-5-[5-(2,4-dichloro-phenoxy)-2-bromo phenoxy ethylene]-2-nitro benzoate and
Tributyl sulfonium-5-(2-chloro-4-trifluoromethyl-phenoxy)-2-nitro benzoate.

In a preferred embodiment of the invention X is a halogen atom, Z is trifluoromethyl group, Y is a hydrogen atom or a halogen atom, A is a nitro group, B contains a sulfonamide group or a carboxy group which can be optionally substituted with $R^3$, wherein the $R^3$ group contains up to a combination of two groupings as previously defined, and each $R^1$ is independently a ($C_1$–$C_4$)alkyl group, preferably a methyl group or an ethyl group. Particularly preferred compounds of this invention are the trimethyl sulfonium and trimethyl sulfoxonium salts of 5-[2-halo-4-(trifluoromethyl)phenoxy]-2-nitrobenzoic acid, trimethyl sulfonium-5-(2-chloro-4-trifluoromethylphenoxy)-2-nitro-N-methanesulfonyl benzamide, trimethyl sulfonium-5-[2-chloro-4-trifluoromethylphenoxy)-2-nitrophenoxy]acetate, trimethyl sulfonium-3-[5-(2-chloro-4-trifluoromethylphenoxy)-2-nitro-phenyl amino]propionate, trimethyl sulfonium-2-chloro-4-trifluoromethyl-3'-[1-(carboxy)-ethoxycarbonyl]-4'-trifluoromethyl-3'-[1-(carboxy)-methoxycarbonyl]-4'nitro diphenyl ether, and trimethyl sulfonium-2-chloro4-trifluoromethyl-3'-[2-(carboxy)-ethoxycarbonyl]-4'nitro diphenyl ether.

The diphenyl ethers of the invention or their precursors can be prepared by reacting a suitably substituted phenol, or the potassium or sodium salt of the phenol, with a suitably substituted halobenzene, such as a chloro- or fluorobenzene, in the presence of an alkaline agent.

The salts of the invention can be prepared by any art-recognized method for producing trialkylsulfonium and trialkylsulfoxonium salts, such as by reacting a trialkylsulfonium or trialkylsulfoxonium halide with the protonated form of the diphenyl ether. It is preferred that the reaction be conducted in the presence of an acid scavenger, e.g., propylene oxide, or a cationic exchange resin. An aqueous medium is used for the reaction. Another solvent may be added to the aqueous medium and suitable solvents include ethers, e.g., diethyl ether, dimethoxyethane, dioxane and tetrahydrofuran, alcohols, e.g., ethanol, dimethyl sulfoxide (DMSO), dimethyl formamide (DMF) and acetonitrile. The particular choice of solvent will depend on the relative solubilities of the starting materials and the resultant salts, and slurries rather than solutions, of certain reagents may be used to obtain the salts. Generally, equivalent amounts of the starting reagents are used and the salt-forming reaction is carried out at about 10° C. to about 100° C. and preferably at about 25° C. to about 45° C. When a cationic exchange resin is utilized, ambient temperature is preferred, Trimethyl sulfonium 5-(2-chloro-4-trifluoro-methyl-phenoxy)-2-nitrobenzoate was prepared by adding an excess of propylene oxide to a solution of trimethyl sulfonium iodide and one equivalent of 5-(2-chloro-4-trifluoromethylphenoxy)-2-nitro benzoic acid in aqueous tetrahydrofuran at 35° C. After 2 hours, the volatile organic compounds were removed under reduced pressure. The remaining aqueous phase was shaken with ether, separated and the water was then removed under reduced pressure to yield trimethyl sulfonium 5-(2-chloro-4-trifluoromethylphenoxy)-2-nitrobenzoate. It was also prepared by regenerating Amberlite 200 cation exchange resin with about 10 equivalents of trimethylsulfonium iodide (Amberlite 200 is a macroreticular, high capacity, strongly acidic cation exchange resin having sulfonic acid functionality, prepared from a styrene divinylbenzene copolymer). Thereafter the column containing the regenerated resin was washed with deionized water and a solution of sodium-5-[2-chloro-4-(trifluoromethyl)phenoxy]-2-nitrobenzoate was then passed down the column to yield trimethylsulfonium 5-(2-chloro-4-trifluoromethyl-phenoxy)-2-nitrobenzoate.

The novel diphenyl ethers of the invention are useful both as preemergence and as postemergence herbicides. Preemergence herbicides are ordinarily used to treat the soil in which the desired crop is to be planted by application either before seeding, during seeding, or, as in most applications, after seeding and before the crop emerges. Postemergence herbicides are those which are applied after the weed plants have emerged and during their growth period.

Among the crops on which the diphenyl ethers of the invention can be advantageously employed are, for example, cotton, soybeans, peanuts, safflower, beans, rice, peas, carrots, corn, wheat and other cereal crops.

Diphenyl ethers of the invention are useful for controlling weeds in rice crops. When used in transplanted rice crops, the ethers can be applied either preemergence or postemergence to the weeds—that is, they can be applied to the growth medium of the transplanted plants either before the weed plants have emerged or while they are in their early stages of growth. The ethers can be applied to the growth medium either before or after the rice has been transplanted to that medium.

The diphenyl ethers of the invention can be applied in any amount which will give the required control of weeds. A preferred rate of application of the herbicides of the invention is from about 0.1 to about 12, and most preferably about 0.25 to 4 pounds of the diphenyl ether per acre.

Under some conditions, the diphenyl ethers of the invention may be advantageously incorporated into the soil or oher growth medium prior to planting a crop. This incorporation can be carried out by any convenient means, including by simple mixing with the soil, by applying the diphenyl ether to the surface of the soil and then disking or dragging into the soil to the desired depth, or by employing a liquid carrier to accomplish the necessary penetration and impregnation.

A diphenyl ether of the invention can be applied to the growth medium or to plants to be treated either by itself or, as is generally done, as a component in a herbicidal composition or formulation which also comprises an agronomically acceptable carrier. By agronomically acceptable carrier is meant any substance which can be used to dissolve, disperse, or diffuse a herbicidal compound in the composition without impairing the effectiveness of the herbicidal compound and which by itself has no detrimental effect on the soil, equipment, crops, or agronomic environment. Mixtures of the diphenyl ethers of the invention may also be used in any of these herbicidal formulations. The herbicidal compositions of the invention can be either solid or liquid formulations or solutions. For example, the diphenyl ethers can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in postemergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual."

The diphenyl ether compounds of this invention can be dissolved in any appropriate solvent. Examples of solvents which are useful in the practice of this invention include water, alcohols, ketones, halogenated hydrocarbons, dimethylformamide, dioxane, dimethyl sulfoxide, and the like. Mixtures of these solvents can also be used. Aromatic hydrocarbons can be added to the solvent to enhance the solubility of the diphenyl ether in the solvent. The concentration of the solution can vary from about 2% to about 98% with a preferred range being about 25% to about 75%.

For the preparation of emulsifiable concentrates, the diphenyl ether can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or ammonium salts of sulfates and sulfonates, alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually about 10% to 60% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98%, preferably about 40% to 75%. A dispersing agent can constitute about 0.5% to about 3% of the composition, and a wetting agent can constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable power with a finely divided carrier. Dust concentrates containing about 20% to 80% of the active ingredient are commonly made and are subsequently diluted to about 1% to 10% use concentration.

Granular formulations can be prepared by impregnating a solid such as granular fuller's earth, vermiculite, ground corn cobs, seed hulls, including bran or other grain-hulls, or similar material. A solution of one or more of the diphenyl ethers in a volatile organic solvent can be sprayed or mixed with the granular solid and the solvent then removed by evaporation. The granular material can have any suitable size, with a preferable size range of 16 to 60 mesh. The diphenyl ether will usually comprise about 2 to 15% of the granular formulation.

The diphenyl ethers of the invention can also be mixed with fertilizers or fertilizing materials before their application. In one type of solid fertilizing composition in which the diphenyl ethers can be used, particles of a fertilizer or fertilizing ingredients, such as ammonium sulfate, ammonium nitrate, or ammonium phosphate, can be coated with one or more of the ethers. The solid diphenyl ethers and solid fertilizing material can also be admixed in mixing or blending equipment, or they can be incorporated with fertilizers in granular formations. Any relative proportion of diphenyl ether and fertilizer can be used which is suitable for the crops and weeds to be treated. The diphenyl ether will commonly be from about 5% to about 25% of the fertilizing composition. These compositions provide fertilizing materials which promote the rapid growth of desired plants, and at the same time control the growth of undesired plants.

The diphenyl ethers of the invention can be applied as herbicidal sprays by methods commonly employed, such as conventional high-gallonage hydraulic sprays, low gallonage sprays, airblast spray, aerial sprays and dusts. For low volume applications a solution of the compound is usually used. The dilution and rate of application will usually depend upon such factors as the type of equipment employed, the method of application, the area to be treated and the type and stage of development of the weeds.

For some applications, it may be desirable to add one or more other herbicides along with diphenyl ethers of the invention. Examples of other herbicides which can be incorporated to provide additional advantages and effectiveness include:

Carboxylic Acids And Derivatives 2,3,6-trichlorobenzoic acid and its salts
2,3,5,6-tetrachlorobenzoic acid and its salts
2-methoxy-3,5,6-trichlorobenzoic acid and its salts
2-methoxy-3,6-dichlorobenzoic acid and its salts
-methyl-3,6-dichlorobenzoic acid and its salts
2,3-dichloro-6-methylbenzoic acid and its salts
2,4-dichlorophenoxyacetic acid and its salts and esters
2,4,5-trichlorophenoxyacetic acid and its salts and esters
2-methyl-4-chlorophenoxyacetic acid and its salts and esters
2-(2,4,5-trichlorophenoxy)propionic acid and its salts and esters
4-(2,4-dichlorophenoxy)butyric acid and its salts and esters
4-(2-methyl-4-chlorophenoxy)butyric acid and its salts and esters
2,3,6-trichlorophenylacetic acid and its salts
3,6-endoxohexahydrophthalic acid
dimethyl 2,3,5,6-tetrachloroterephthalate
trichloroacetic acid and its salts
2,2-dichloropropionic acid and its salts
2,3-dichloroisobutyric acid and its salts Carbamic Acid Derivatives
ethyl N,N-di(n-propyl)thiolcarbamate
propyl N,N-di(n-propyl)thiolcarbamate
ethyl N-ethyl-N-(n-butyl)thiolcarbamate
propyl N-ethyl-N-(n-butyl)thiolcarbamate
2-chloroallyl N,N-diethyldithiocarbamate
N-methyldithiocarbamic acid salts
ethyl 1-hexamethyleneiminecarbothiolate
isopropyl N-phenylcarbamate
isopropyl N-(m-chlorophenyl)carbamate
4-chloro-2-butynyl N-(m-chlorophenyl)carbamate
methyl N-(3,4-dichlorophenyl)carbamate

Phenols dinitro-o-(sec-butyl)phenol and its salts
pentachlorophenol and its salts

Substituted Ureas (3,4-dichlorophenyl)-1,1-dimethylurea
3-phenyl-1,1-dimethylurea
3-(3,4-dichlorophenyl)-3-methoxy-1,1-dimethylurea
3(4-chlorophenyl)-3-methoxy-1,1-dimethylurea
3-(3,4-dichlorophenyl)-2-n-butyl-1-methylurea
(3,4-dichlorophenyl)-1-methoxy-1-methylurea
33-(4-chlorophenyl)-1-methoxy-1-methylurea
3-(3,4-dichlorophenyl)-1,1,3-trimethylurea
3-(3,4-dichlorophenyl)-1,1-diethylurea dichloral urea

Substituted Triazines 2-chloro-4,6-bis(ethylamino)-2-triazine
2-chloro-4-ethylamino-6-isopropylamino-s-triazine
2-chloro-4,6-bis(methoxypropylamino)-2-triazine
2-methoxy-4,6-bis(isopropylamino)-s-triazine
2-chloro-4-ethylamino-6-(3-methoxypropylamino)-s-triazine
2-methylmercapto-4,6-bis(isopropylamino)-s-triazine
2-methylmercapto-4,6-bis(ethylamino)-s-triazine
2-methylmercapto-4-ethylamino-6-isopropylamino-s-triazine
2-chloro-4,6-bis(isopropylamino)-s-triazine
2-methoxy-4,6-bis(ethylamino)-s-triazine
2-methoxy-4-ethylamino-6-isopropylamino-s-triazine
2-methylmercapto-4-(2-methoxyethylamino)-6-isopropyl-amino-s-triazine

Diphenyl Ether Derivatives 2,4-dichloro-4'-nitrodiphenyl ether
2,4,6-trichloro-4'-nitrodiphenyl ether
2,4-dichloro-6-fluoro-4'-nitrodiphenyl ether
3-methyl-4'-nitrodiphenyl ether
3,5-dimethyl-4'-nitrodiphenyl ether
2,4'-dinitro-4-trifluoromethyldiphenyl ether
2,4-dichloro-3'-methoxy-4'-nitrodiphenyl ether
2-chloro-4-trifluoromethyl-3'-[2-(hydroxycarbonyl)ethoxycarbonyl]-4'-nitro diphenyl ether
2-chloro-4-trifluoromethyl-3'-[1-(methoxycarbonyl)ethoxycarbonyl]-4'-nitrodiphenyl ether
2-chloro-4-trifluoromethyl-3'-[(ethoxycarbonyl)methoxycarbonyl]-4'-nitrodiphenyl ether
5-(2-chloro-4-trifluoromethylphenoxy)-2-nitro-N-methanesulfonyl benzamide

Anilides

N-(3,4-dichlorophenyl)propionamide
N-(3,4-dichlorophenyl)methacrylamide
N-(3-chloro-4-methylphenyl)-2-methylpentanamide
N-(3,4-dichlorophenyl)trimethylacetamide
N-(3,4-dichlorophenyl)-a,a-dimethylvaleramide
N-isopropyl-N-phenylchloroacetamide
N-n-butoxymethyl-N-(2,6-diethylphenyl)-chloroacetamide
N-n-methoxymethyl-N-(2,6-diethylphenyl)-chloroacetamide

Uracils 5-bromo-3-s-butyl-6-methyluracil
5-bromo-3-cyclohexyl-1,6-dimethyluracil
3-cyclohexyl-5,6-trimethyleneuracil
5-bromo-3-isopropyl-6-methyluracil
3-tert-butyl-5-chloro-6-methyluracil

Nitriles 2,6-dichlorobenzonitrile diphenylacetonitrile
3,5-dibromo-4-hydroxybenzonitrile
3,5-diiodo-4-hydroxybenzonitrile

Other Organic Herbicides 2-chloro-N,N-diallylacetamide
N-(1,1-dimethyl-2-propynyl)-3,5-dichlorobenzamide
maleic hydrazide
3-amino-1,3,4-triazole monosodium methanearsonate
disodium methanearsonate
N,N-dimethyl-a,a-diphenylacetamide
N,N-di(n-propyl)-2,6-dinitro-4-trifluoromethylaniline
N,N-di(n-propyl)-2,6-dinitro-4-methylaniline
N,N-di(n-propyl)-2,6-dinitro-4-methylsulfonylaniline
O-(2,4-dichlorophenyl)-O-methyl-isopropylphosphoramido-thioate
4-amino-3,5,6-trichloropicolinic acid
2,3-dichloro-1,4-naphthoquinone di(methoxythiocarbonyl)disulfide
3-isopropyl-1H-2,1,3-benzothiadiazin-(4)3H-one-2,2-dioxide
6,7-dihydrodipyridol[1,2-a:2',1'-c]pyrazidinium salts
1,1'-dimethyl-4,4'-bipyridinium salts
3,4,5,6-tetrahydro-3,5-dimethyl-2-thio-2H-1,3,5-thiadiazine
2-chloro-N-[(4-methoxy-6-methyl-1,3,5-triazin-2-yl)amino carbonyl]benzene sulfonamide
2-(1-allyloxyamino-butylidine)-4-carbomethoxy-5-dimethyl-cyclohexan-1,3-dione
2-(1-ethoxyamino-butylidine)-5-(2-ethylsulfinyl-propyl)-cyclohexan-1,3-dione
Butyl-2-[4-(4-trifluoromethyl-2pyridyloxy)phenoxy]-propionate.

When mixtures of herbicides are employed, the relative proportions which are used will depend upon the crop to be treated and the degree of selectivity in weed control which is desired.

What is claimed is:
1. A compound of the formula

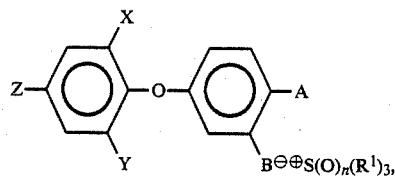

wherein:

X and Y are independently a hydrogen atom, a halogen atom, a trifluoromethyl group, an alkyl group or a cyano group;

Z is a halogen atom, a trifluoromethyl group, an alkyl group, a cyano group or —S(O)$_m$R wherein m is 0, 1 or 2 and R is an alkyl group;

A is a halogen atom, a nitro group or a cyano group;

B is a negatively charged organic radical selected from the group consisting of a carboxy group, —COO$\ominus$, a sulfonamide group, C(O)N$\ominus$SO$_2$R$^3$, and a R$^3$ organic moiety substituted with a carboxy group, —R$^3$CO$_2\ominus$, or a sulfonamide group, —R$^3$C(0)NSO$_2$R$^3$, wherein R$^3$ is an organic radical containing an alkyl group, alkenyl group, alkynyl group, alkylamino group, alkoxy group, aryl group, carbalkyl group, hydroxyalkyl group, alkoxyalkyl group, haloalkyl group, aryl group, alkylaryl group, a substituted aryl group or a substituted alkylaryl group having up to two substitutions wherein the substitution is selected from the group consisting of a halogen atom, a trifluoromethyl group, a cyano group, a nitro group, a carboxyalkyl group, an alkoxy group, an alkyl group, an alkenyl group, an alkynyl group, a thioalkyl group, a phosphite group and an amino group;

S is sulfur;
O is oxygen;
n is 0 or 1; and
R$^1$ is an alkyl group, an aryl group or —N(R$^2$)$_2$ wherein R$^2$ is an alkyl group or an aryl group.

2. The compound of claim 1 wherein the B substituent contains a sulfonamide group or a carboxy group.

3. The compound of claim 2 wherein X and Y are independently a hydrogen atom, a halogen atom or a trifluoromethyl group; Z is a halogen atom or a trifluoromethyl group; and A is a halogen atom or a nitro group.

4. The compound of claim 3 wherein X is a halogen atom, Y is a hydrogen atom or a halogen atom, Z is a trifluoromethyl group and A is a nitro group.

5. The compound of claim 3 or claim 4 wherein the B substituent is selected from the group consisting of a carboxy group, —COO$\ominus$, a sulfonamide group, C(O)N$\ominus$SO$_2$R$^3$, and a R$^3$ organic moiety substituted with a carboxy group, —R$^3$CO$_2\ominus$, or a sulfonamide group, —R$^3$C(O)NSO$_2$R$^3$, wherein R$^3$ is an organic radical containing an alkyl group, alkenyl group, alkynyl group, alkylamino group, alkoxy group, aryl group, carbalkyl group, hydroxyalkyl group, alkoxyalkyl group, haloalkyl group, aryl group, alkylaryl group, a substituted aryl group or a substituted alkylaryl group having up to two substitutions wherein the substitution is selected from the group consisting of a halogen atom, a trifluoromethyl group, a cyano group, a nitro group, a carboxyalkyl group, an alkoxy group, an alkyl group, an alkenyl group, an alkynyl group, a thioalkyl group, a phosphite group and an amino group.

6. The compound of claim 5 wherein X is a chlorine atom and Y is a hydrogen atom and the aryl or aralkyl group has up to one substitution.

7. The compound of claim 6 wherein R$^1$ is an alkyl group containing from one to four carbon atoms.

8. A compound selected from the group consisting of trialkyl sulfonium, trialkyl sulfoxonium and dialkylamino sulfoxonium salts of 5-(2-chloro-4-trifluoromethylphenoxy)-2-nitrobenzoic acid, 2-chloro- 4-trifluoromethyl-3'(2-(carboxy)-ethoxycarbonyl)-4'-nitro-diphenyl ether, 2-chloro-4-trifluoromethyl-3'-(1-carboxy)-methoxycarbonyl)-4'-nitro diphenyl ether and 2-chloro-4-trifluoromethyl-3'(2-(carboxy)-ethoxycarbonyl)-4'-nitrodiphenyl ether.

9. The compound of claim 8 wherein the compound is selected from the group consisting of trimethyl sulfonium and trimethyl sulfoxonium salts of 5-(2-chloro-4-(trifluoromethyl)phenoxy)-2-nitro benzoic acid.

10. A method of controlling weeds comprising applying to the surface of the growth medium prior to the emergence of the weeds from the growth medium the compound of claim 1 in an amount sufficient to control the growth of the weeds.

11. A method of controlling weeds comprising applying to the weeds during a growth period the compound of claim 1 in an amount sufficient to control the growth of the weeds.

12. The method of claim 10 or claim 11 wherein the compound is applied at a rate of about 0.1 to about 12 pounds per acre.

13. A herbicide composition comprising the compound of claim 1 and an agronomically acceptable carrier.

14. A herbicide composition comprising the compound of claim 8 and an agronomically acceptable carrier.

15. A compound of the formula

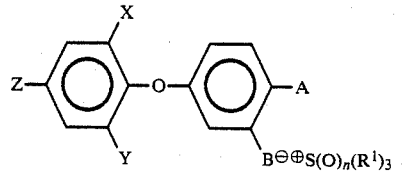

wherein:

X and Y are independently a hydrogen atom, a halogen atom, a trifluoromethyl group, an alkyl group or a cyano group;

Z is a halogen atom, a trifluoromethyl group, an alkyl group, a cyano group or —S(O)$_m$R wherein m is 0, 1 or 2 and R is an alkyl group;

A is a halogen atom, a nitro group or a cyano group;

B is a negatively charged organic radical selected from the group consisting of a carboxy group, —COO$^\ominus$, and a R$^3$ organic moiety substituted with a carboxy group, —R$^3$CO$_2^\ominus$, or a sulfonamide group, —R$^3$C(O)N$^\ominus$SO$_2$R$^3$, wherein R$^3$ is an organic radical containing an alkyl group, alkenyl group, alkynyl group, alkylamino group, alkoxy group, aryl group, haloalkyl group, aryl hydroxyalkyl group, alkoxyalkyl group, haloalkyl group, aryl group, alkylaryl group, a substituted aryl group or a substituted alkylaryl group having up to two substitutions wherein the substitution is selected from the group consisting of a halogen atom, a trifluoromethyl group, a cyano group, a nitro group, a carboxyalkyl group, an alkoxy group, an alkyl group, an alkenyl group, an alkynyl group, a thioalkyl group, a phosphite group and an amino group;

S is sulfur;

O is oxygen;

n is 0 or 1; and

R$^1$ is an alkyl group, an aryl group or —N(R$^2$)$_2$ wherein R$^2$ is an alkyl group or an aryl group.

16. The compound of claim 15 wherein X and Y are independently a hydrogen atom, a halogen atom or a trifluoromethyl group; z is a halogen atom or a trifluoromethyl group; and A is a halogen atom or a nitro group.

17. The compound if claim 16 wherein X is a halogen atom, Y is a hydrogen atom or a halogen atom, Z is a trifluoromethyl group and A is a nitro group.

18. The compound of claim 15 wherein X is a chlorine atom and Y is a hydrogen atom and the aryl or aralky group has up to one substitution.

19. The compound of claim 18 wherein R$^1$ is an alkyl group containing from one to four carbon atoms.

20. A method of controlling weeds comprising applying to the surface of the growth medium prior to the emergence of the weeds from the growth medium the compound of claim 15 is an amount sufficient to control the growth of the weeds.

21. A method of controlling weeds comprising applying to the weeds during a growth period the compound of claim 15 in an amount sufficient to control the growth of the weeds.

22. The method of claim 20 or claim 21 wherein the compound is applied at a rate of about 0.1 to about 12 pounds per acre.

23. A herbicide composition comprising the compound of claim 15 and an agronomically acceptable carrier.

24. A compound of the formula

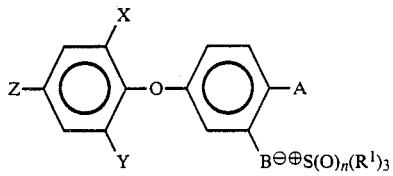

wherein:

X and Y are independently a hydrogen atom, a halogen atom, a trifluoromethyl group, an alkyl group or a cyano group;

Z is a halogen atom, a trifluoromethyl group, an alkyl group, a cyano group or —S(O)$_m$R wherein m is 0, 1 or 2 and R is an alkyl group;

A is a halogen atom, a nitro group or a cyano group;

B is a negatively charged organic radical selected from the group consisting of a carboxy group, —COO$^\ominus$, and a R$^3$ organic moiety substituted with a carboxy group, —R$^3$CO$_2^\ominus$, wherein R$^3$ is an organic radical containing an alkyl group, alkenyl group, alkynyl group, alkylamino group, alkoy group, aryl group, carbalkyl group, hydroxyalkyl group, alkoxyalkyl group, haloalkyl group, aryl group, alkylaryl group, a substituted aryl group or a substituted alkylaryl group having up to two substitutions wherein the substitution is selected from the group consisting of a halogen atom, a trifluoromethyl group, a cyano group, a nitro group, a carboxyalkyl group, an alkoxy group, an alkyl group, an alkenyl group, an alkynyl group, a thioalkyl group, a phosphite group and an amino group;

S is sulfur;

0 is oxygen;

n is 0 or 1; and

R$^1$ is an alkyl group, an aryl group or —N(R$^2$)$_2$ wherein R$^2$ is an alkyl group or an aryl group.

25. The compound of claim 25 wherein X and Y are independently a hydrogen atom, a halogen atom or a trifluoromethyl group; Z is a halogen atom or a trifluoromethyl group; and A is a halogen atom or a nitro group.

26. The compound of claim 25 wherein X is a halogen atom, Y is a hydrogen atom or a halogen atom, Z is a trifluoromethyl group and A is a nitro group.

27. The compound of claim 24 wherein X is a chlorine atom and Y is a hydrogen atom and the aryl or aralkyl group has up to one substitution.

28. The compound of claim 27 wherein R$^1$ is an alkyl group containing from one to four carbon atoms.

29. A method of controlling weeds comprising applying to the surface of the growth medium prior to the emergence of the weeds from the growth medium the compound of claim 24 in an amount sufficient to control the growth of the weeds.

30. A method of controlling weeds comprising applying to the weeds during a growth period the compound of claim 24 in an amount sufficient to control the growth of the weeds.

31. The method of claim 29 or claim 30 wherein the compound is applied at a rate of about 0.1 to about 12 pounds per acre.

32. A herbicide composition comprising the compound of claim 24 and an agronomically acceptable carrier.

* * * * *

UNITED STATES PATENT AND TRADEMARK OFFICE
CERTIFICATE OF CORRECTION

PATENT NO. : 4,806,682

DATED : February 21, 1989

INVENTOR(S) : Roy Y. Yih

It is certified that error appears in the above-identified patent and that said Letters Patent is hereby corrected as shown below:

Claim 15, column 11, line 17, delete "haloalkyl group, aryl" and insert --carbalkyl group,--

Claim 25, column 12, line 40, delete "25" and insert --24--

Signed and Sealed this

Fourth Day of December, 1990

Attest:

HARRY F. MANBECK, JR.

*Attesting Officer*  *Commissioner of Patents and Trademarks*